United States Patent [19]

Creps

[11] Patent Number: 4,968,252
[45] Date of Patent: Nov. 6, 1990

[54] SUPPORT FOR DENTAL INSTRUMENT

[76] Inventor: Georges Creps, 11, Place de la Résistance, 14300 Caen, France

[21] Appl. No.: 214,360
[22] Filed: Jul. 1, 1988
[30] Foreign Application Priority Data Jul. 23, 1987 [FR] France ............................... 87 10481

[51] Int. Cl.⁵ .................................................. A61C 3/00
[52] U.S. Cl. ....................................... 433/229; 433/141
[58] Field of Search ................... 433/27, 75, 114, 229, 433/28, 141; 128/670, 671, 672

[56] References Cited

U.S. PATENT DOCUMENTS

| | | | |
|---|---|---|---|
| 4,409,616 | 10/1983 | Ledley | 385/111 |
| 4,446,453 | 5/1984 | Eenboom et al. | 340/286.13 |
| 4,557,693 | 12/1985 | Elggren | 433/229 |
| 4,655,712 | 4/1987 | Croll | 433/229 |
| 4,832,599 | 5/1989 | Kung | 433/32 |

FOREIGN PATENT DOCUMENTS 3345465  6/1985  Fed. Rep. of Germany .

Primary Examiner—John J. Wilson
Attorney, Agent, or Firm—Beveridge, DeGrandi & Weilacher

[57] ABSTRACT

An apparatus for dentistry which includes an information system having a program for generating data in a sequential manner, a handle device, and an information link which allows for the introduction of data from the information system to the handle device. The handle device includes a display unit as well as a data input key. The data input key, upon being manipulated, chooses a data item derived from the information system and the display unit displays at least the last data item introduced or the data item being introduced. The data being introduced is segmetized into discrete groups and a data item from each group can be chosen upon manipulation of the data input key and the display unit can include a plurality of display segments for displaying data items chosen from the segmetized groups of data. Audible signals can also be used in association with displaying data items.

23 Claims, 1 Drawing Sheet

SUPPORT FOR DENTAL INSTRUMENT

BACKGROUND OF THE INVENTION

1. Field of the Invention

This invention relates to a support for a dental instrument incorporating simplified means for input and for output of data connectable to an information system.

This invention also relates to the art of dentistry as well as stomatological medicine, and, more particularly, the formulation of a patient record card or of an administrative document corresponding to a clinical or paradontological examination, or alternatively a treatment or proposed treatment.

2. Background Discussion

Customarily, when a dental surgeon or a stomatologist undertakes the examination of a patient, he is obliged to make use of the services of an assistant or of a secretary to complete the record card or the document in accordance with information provided by him, and, when he has no assistance available, he is obliged, in order to make a note himself of each item of information, to put down his dental instrument and to remove his eyes from his field of action; this results in a great loss of time.

Information programs are known, which permit the input and the processing of the dental data, but nevertheless without solving the aforementioned problem, since utilization thereof likewise necessitates the employment of an assistant or putting down the instrument and leaving the field of action repeatedly.

SUMMARY OF THE INVENTION

The object of the invention is to eliminate the aforementioned disadvantages by providing an apparatus which permits the dental surgeon or the stomatologist to enter his dental data himself in an information system without releasing the dental instrument employed or removing his eyes from the field of action.

The invention consists in providing a supporting handle, at the end of which there may be removably mounted the desired instrument, such as probe, mirror or light, this support moreover comprising at least one data input key and a window for the local display at least of the last data, as well as an information link with the information system used.

In particular, with a single command key and a relatively simple segmental display unit, it is possible to solve the problem in a manner which is particularly effective and has a low space requirement.

BRIEF DESCRIPTION OF THE PREFERRED EMBODIMENTS

Further particular features of the invention will appear in the description, which will follow, of an embodiment taken by way of example and represented in the accompanying drawing, in which.

DETAILED DESCRIPTION OF THE PREFERRED EMBODIMENTS

Figure 1:
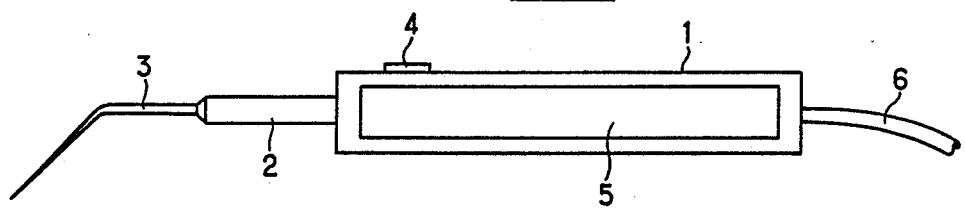
FIG. 1 is a diagrammatic overall view of the instrument.

The supporting handle 1 according to the invention comprises, above all, a support 2 for the removable fixing of a dental instrument 3 of known type, such as a probe, a mirror or a light, this instrument being intended to permit the examination.

The supporting handle 1 comprises, on the other hand, a data input key 4 situated in a good position to be activated easily by a finger of the practitioner, and likewise a window 5 permitting the observation of a local display unit for the representation of the data, or at least of the last data item introduced, in order to restrict the space requirement.

Finally, the supporting handle 1 comprises a means for an information link with the information system employed. In the example represented, this means consists of an electrical supply and linking cable 6, but it would be possible advantageously to use likewise a battery power supply and an information link by means of a radio, infrared or ultrasonic transmitter/receiver.

In this way, the practitioner, especially the dentist or the stomatologist, can, while investigating the mouth of his patient by means of his instrument 3, enter the corresponding data by the key 4 and monitor, by the display unit 5, the accuracy of these data, without having to put down the entire instrument or to remove his eyes from his field of action.

The apparatus according to the invention is, of course, used in conjunction with an information system ensuring the acquisition and the processing of the data as well as the complete representation of them, for example on a video screen and/or on a printer.

The use of a single command key 4 is possible by virtue of a sequential programming of the information system, while the local display unit 5, which is of necessarily small format, may be of a relatively simple type and may display only the last data item introduced or in the course of introduction.

This display unit 5 may be of the matrix type, but it is more advantageous to use a display unit of the segmental type, which is not only more economical, but reduces to a very great extent the space requirement of the local operating circuits which are necessarily carried by the supporting handle 1.

Figure 2:
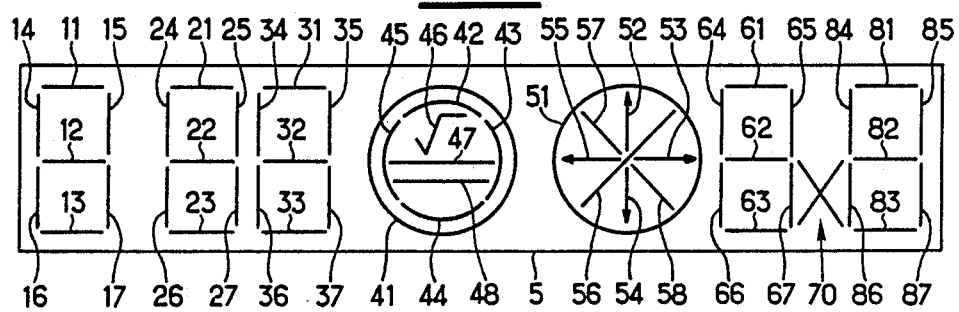
FIG. 2 represents an example of a segmental display unit.

By way of example, FIG. 2 shows a relatively simple segmentation which permits, with a small number of segments, the formation of all the letters, figures and symbols which are required.

Figure 3:
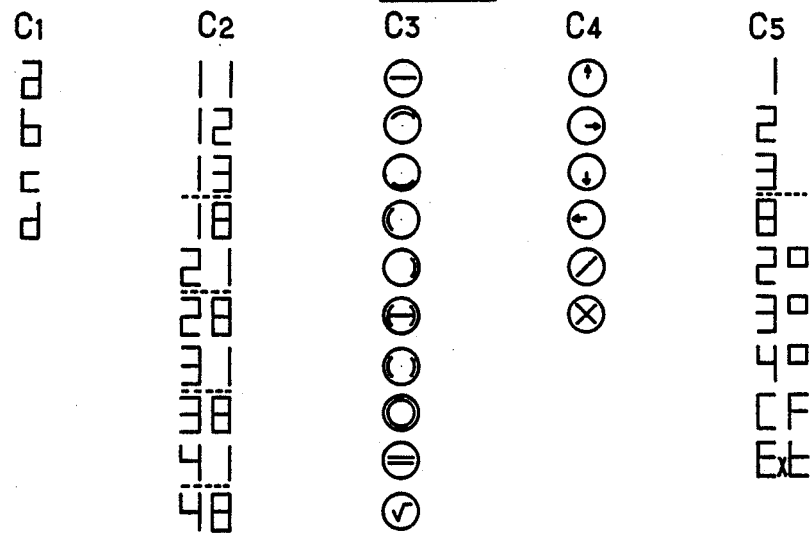
FIG. 3 represents, opposite FIG. 2, the symbols which it is possible to display.

The first group of segments from 11 to 17 is a representation having seven conventional segments, and the selective excitation of these segments, be they photoemitting diodes or liquid crystals, permits the display of one of the letters a, b, c and d, as represented in the column C1 of FIG. 3. This letter permanently represents the program chosen, preferably by a direct command to the keyboard of the information system, the four programs a, b, c and d corresponding respectively to the clinical examination, to the paradontological examination, to an indication of treatment or to a proposed treatment, for example for a preliminary request for a prosthesis.

The segments 21 to 37 form two figures with seven conventional segments permitting the display, in accordance with the universal coding, of the number of the tooth, by means of the FIGS. 11 to 18, 21 to 28, 31 to 38 and 41 to 48 for adults, or alternatively the figures 51 to 85 for the temporary teeth of children. In the column C2 of FIG. 3, only the first of these numbers which are most usual have been shown.

The special segments 41 to 48 permit the display of the symbols represented in column C3 of FIG. 3. The first seven correspond to the representation of the position of one or of several fillings on the tooth under consideration, while the seventh symbol represents a crown, the eighth a bridge and the ninth a root. In the same way, the group of special segments 51 to 58 permits the display of the symbols of the column C4 of FIG. 3, namely four position arrows and diagonal signs: / and X.

Finally, the last group of segments, 61 to 87, comprises respectively two groups of seven segments, 61 to 67 and 81 to 87, separated by a single segment 70 in the shape of a cross of St. Andrew. This assembly permits the display of the symbols represented in the column C5 of FIG. 3.

For a sequential programming, it is necessary to select an order of succession among the 32 teeth of a complete adult set of teeth. This order may, for example, be the order of the increasing figures, but it may just as easily be a continuous order, for example from left to right, and consequently proceed from the numbers 18 to 11, then 21 to 28, followed by 38 to 31 and finally 41 to 48.

If the practitioner has selected the program a, that is to say the clinical examination, after the appearance on the segments 21 to 37 of the number of the first tooth in the order selected hereinabove, the segments 41 to 48 display sequentially, at a determined rate, the nine symbols of the column C3, until the practitioner presses on the key 4 in order to select that one of the symbols which is appropriate. Preferably, at the start of this sequence, there is a "nil" time interval when everything is extinguished, or only the segment 41 is then excited; this permits the display of no symbol whatsoever and passing to the following tooth. Conversely, if the sequence is terminated without the practitioner having pressed on a key 4, the sequence recommences cyclically, still with the same tooth number.

In consequence, once the practitioner has pressed on the key 4 to select the desired symbol, the corresponding data item is transmitted to the computer and the segments 21 to 37 display the following tooth, and so on. At each instant, the practitioner can therefore monitor on his local window the progress of the input of data, and at the same time the video screen, with which the information system is generally equipped, permanently displays the complete trace of the two jaws with the corresponding symbol inscribed in the correct position, the entire trace being reupdated in the course of the execution of the program which can be repeated if necessary.

If the practitioner has selected the program b for paradontological examination, it is the segments 51 to 55 which are used to display the position arrow symbol (the first four symbols of the column C4) followed by a figure obtained by the segments 61 to 67, this figure indicating the depth of the paradontal pockets in millimeters, from 1 to 7 or from 1 to 8 in the position indicated by the arrows.

In the case of this program, there is, on the other hand, a difference as compared with the program a which arises as a result of the fact that the selection of an arrow and of a figure does not necessarily terminate the sequence, since it may be necessary to inscribe a plurality of depths for an individual tooth, up to four corresponding to the four arrows. The simplest means consists in causing each one of the arrow symbols to be followed successively by the successive figures from 1 to 8; this makes a sequence of 32 positions, plus one which corresponds to the nil indication when no symbol has to be inscribed.

Nevertheless, in order to gain time, this sequence may be divided into two subsequences, the first displaying the arrow direction, and then, after selection by the key 4, a second sequence corresponding to the figure. The selection of the corresponding figure or of the nil position by means of the key 4 permits jumping of the last figures of the subsequence, but does not pass to the following tooth, but to the following arrow position of the sequence of arrows. Accordingly, it is not until after exhaustion of the sequence of arrows that the change takes place to the following tooth. If the nil position of the depth figures is at the start of the sequence, it is therefore possible to jump each arrow position by pressing in two successive strokes; this is very rapid. Naturally, in this case again, the data are progressively transmitted to the computer and the trace consequently reupdated.

If the practitioner has selected the program c for indication of treatment, in this case each sequence corresponding to a tooth number utilizes the last five symbols of the column C5 corresponding respectively to an indication of treatment in the second degree, third degree or fourth degree, an indication of a cap or an indication of extraction. The procedure thus involves the performance of a simple sequence as in the case of the program a.

Finally, if the practitioner has selected the program d, that is to say a request for a preliminary arrangement for a prosthesis, the sequence relating to each tooth number is even simpler, since it comprises only the last two symbols of the column C4, utilizing exclusively the segments 51, 56, 57 and 58.

Naturally, once the data have been entered, monitored and displayed, they can be supplemented by any useful indication, especially the name of the patient, and can generate the production, by means of a printer, of any paper document, such as a record card or administrative document, as well as possibly an input on an information file for a subsequent utilization.

By way of a variant, the display of the various indicated symbols corresponding to the various phases of the four programs may be duplicated by the emission of audible signals, which may range from the simple beep to the complete enumeration of the various phases of each sequence by a voice synthesizer device.

I claim:
1. An apparatus for use with a dental instrument, comprising:
   an information system which includes a program for generating data in a sequential manner;
   information link means;
   handle means provided with at least one data input key and a display unit, said information link means including means for introducing data items from said information system to said handle means in a sequential fashion, and said display unit including means for displaying at least the last data item introduced or the data item in the course of introduction through manipulation of said data input key, and said handle means further including connection means for removably fixing a dental instrument.

2. An apparatus as recited in claim 1 wherein said information system comprises segmetizing means for segmetizing into discrete groups the data items being introduced sequentially.

3. An apparatus as recited in claim 2 wherein said display unit displays in sequential fashion data items contained within said discrete groups.

4. An apparatus as recited in claim 3 wherein said display unit, upon manipulation of said data input key, displays, in fixed fashion, a data item.

5. An apparatus as recited in claim 4 wherein said display means includes a plurality of display segments corresponding with said segmented discrete data groups.

6. An apparatus as recited in claim 1 wherein said display means, upon manipulation of said data input key, displays in fixed fashion a data item.

7. An apparatus as recited in claim 1 further comprising audible signal generating means which assigns an audible signal to each data item and generates the audible signal upon a data item being received by said handle means.

8. An apparatus for the art of dentistry, comprising:
a dental instrument specifically adapted for dental treatment;
an information system which includes a program for generating data in a sequential manner;
information link means;
handle means provided with at least one data input key and a display unit, said information link means including means for introducing data items from said information system to said handle means in a sequential fashion, and said display unit including means for displaying at least the last data item or the data item currently introduced through manipulation of said data input key, and said handle means further including connection means for removably fixing said dental instrument.

9. An apparatus as recited in claim 8, wherein said information system includes segmetizing means for segmetizing into discrete groups said data items being introduced sequentially.

10. An apparatus as recited in claim 9 wherein said display unit displays, in sequenced fashion, data items contained within said discrete groups.

11. An apparatus as recited in claim 10 wherein said display unit, upon manipulation of said data input key displays, in fixed fashion, a data item.

12. An apparatus as recited in claim 11 wherein a plurality of data items are displayed in fixed fashion and each of said data items being displayed in fixed fashion by said display unit represents a data item chosen from a respective one of said discrete groups.

13. An apparatus as recited in claim 8 further comprising audible signal generating means which assigns an audible signal to each data item and generates the audible signal upon a data item being displayed by said display means.

14. An apparatus for the art of dentistry, comprising:
means for outputting a plurality of data choices sequentially,
handle means having means for receiving data choices sequentially from said means for outputting a plurality of data choices sequentially, said handle means including at least one data input key, said handle means further including display means for displaying said data choices and for displaying at least one data choice in fixed fashion upon manipulation of said data input key, and connection means for connectably receiving a dental instrument.

15. An apparatus as recited in claim 14, wherein said connecting means includes means for releasably holding the dental instrument.

16. An apparatus as recited in claim 14 wherein said means for outputting comprises segmetizing means for segmetizing said data choices being outputted sequentially into discrete groups.

17. An apparatus as recited in claim 16, wherein one discrete group of displayed data choices includes a plurality of indicia members with said indicia members including representations of filled teeth locations.

18. An apparatus as recited in claim 17 wherein a second discrete group of displayed data choices includes a plurality of indicia members with at least some of said indicia members being direction arrows.

19. An apparatus as recited in claim 16 wherein said display means, upon sequential manipulation of said data input key, displays, in fixed fashion, a plurality of data choices.

20. An apparatus as recited in claim 19 wherein said display means includes a plurality of display segments corresponding with said discrete data groups.

21. An apparatus as recited in claim 14 wherein said display means, upon sequential manipulation of said data input key, displays, in fixed fashion, a plurality of data choices.

22. An apparatus as recited in claim 14 further comprising audible signal generating means which assigns an audible signal to each data choice and generates the audible signal upon a data item being displayed.

23. An apparatus as recited in claim 14 further comprising a dental instrument connected with said connecting means.

* * * * *